(12) United States Patent
Gu et al.

(10) Patent No.: US 10,774,177 B2
(45) Date of Patent: Sep. 15, 2020

(54) CYCLIC ESTER DUAL CURE RESINS FOR ADDITIVE MANUFACTURING

(71) Applicant: Carbon, Inc., Redwood City, CA (US)

(72) Inventors: Xinyu Gu, Shanghai (CN); Jason P. Rolland, San Carlos, CA (US)

(73) Assignee: Carbon, Inc., Redwood City, CA (US)

( * ) Notice: Subject to any disclaimer, the term of this patent is extended or adjusted under 35 U.S.C. 154(b) by 0 days.

(21) Appl. No.: 16/674,702

(22) Filed: Nov. 5, 2019

(65) Prior Publication Data

US 2020/0079898 A1 Mar. 12, 2020

Related U.S. Application Data

(63) Continuation of application No. 15/361,644, filed on Nov. 28, 2016, now Pat. No. 10,501,572.

(60) Provisional application No. 62/270,646, filed on Dec. 22, 2015.

(51) Int. Cl.

| | | |
|---|---|---|
| *B29C 67/00* | (2017.01) | |
| *H05B 6/00* | (2006.01) | |
| *C08F 2/50* | (2006.01) | |
| *C08G 63/08* | (2006.01) | |
| *B33Y 10/00* | (2015.01) | |
| *B33Y 80/00* | (2015.01) | |
| *B33Y 70/00* | (2020.01) | |
| *A61L 31/14* | (2006.01) | |
| *A61L 31/16* | (2006.01) | |
| *A61L 27/58* | (2006.01) | |
| *A61L 27/54* | (2006.01) | |
| *A61K 9/00* | (2006.01) | |
| *C08G 63/78* | (2006.01) | |
| *B29C 64/129* | (2017.01) | |
| *B29C 35/08* | (2006.01) | |
| *B29K 33/04* | (2006.01) | |
| *B29L 31/00* | (2006.01) | |

(52) U.S. Cl.
CPC ............ *C08G 63/08* (2013.01); *A61K 9/0021* (2013.01); *A61K 9/0051* (2013.01); *A61L 27/54* (2013.01); *A61L 27/58* (2013.01); *A61L 31/148* (2013.01); *A61L 31/16* (2013.01); *B29C 64/129* (2017.08); *B33Y 10/00* (2014.12); *B33Y 70/00* (2014.12); *B33Y 80/00* (2014.12); *C08G 63/78* (2013.01); *A61L 2430/02* (2013.01); *B29C 2035/0833* (2013.01); *B29C 2035/0855* (2013.01); *B29K 2033/04* (2013.01); *B29K 2995/006* (2013.01); *B29L 2031/7532* (2013.01)

(58) Field of Classification Search
CPC ......... C08G 63/08; C08G 63/78; A61L 27/58; A61L 27/54; A61L 31/16; A61L 31/148; A61L 2430/02; B29L 2995/006; B29L 2033/04; A61K 9/0051; A61K 9/0021; A61K 9/0024; B33Y 70/00; B33Y 10/00; B33Y 80/00; B29C 64/129
USPC .......... 264/489, 405; 522/6, 71, 189, 184, 1; 520/1
See application file for complete search history.

(56) References Cited

U.S. PATENT DOCUMENTS

| | | | |
|---|---|---|---|
| 4,173,682 A | 11/1979 | Noomen et al. | |
| 4,389,514 A | 6/1983 | Schmidle et al. | |
| 4,421,822 A * | 12/1983 | Levens | C08F 2/46 428/343 |
| 4,632,975 A | 12/1986 | Cornell et al. | |
| 5,236,637 A | 8/1993 | Hull | |
| 5,264,061 A | 11/1993 | Juskey et al. | |
| 5,298,532 A | 3/1994 | Ali | |
| 5,391,072 A | 2/1995 | Lawton et al. | |
| 5,418,112 A | 5/1995 | Mirle et al. | |
| 5,529,473 A | 6/1996 | Lawton et al. | |
| 5,629,133 A | 5/1997 | Wolf et al. | |
| 5,674,921 A | 10/1997 | Regula et al. | |
| 5,679,719 A | 10/1997 | Klemarczyk et al. | |
| 5,695,708 A | 12/1997 | Karp et al. | |
| 5,856,382 A | 1/1999 | Ohrbom et al. | |
| 6,309,797 B1 | 10/2001 | Grinevich et al. | |
| 7,438,846 B2 | 10/2008 | John | |
| 7,892,474 B2 | 2/2011 | Shkolnik et al. | |
| 8,110,135 B2 | 2/2012 | El-Siblani | |
| 8,980,971 B2 | 3/2015 | Ueda et al. | |
| 9,120,270 B2 | 9/2015 | Chen et al. | |
| 9,205,601 B2 | 12/2015 | Desimone et al. | |

(Continued)

FOREIGN PATENT DOCUMENTS

| | | |
|---|---|---|
| CN | 103571211 | 2/2014 |
| EP | 0525578 | 2/1993 |

(Continued)

OTHER PUBLICATIONS

Murayama et al. "Anionic Ring-Opening Polymerization of a Cyclic Carbonate Having a Norbornene Structure with Amine initiators" Macromolecules, 31(3):919-923 (1998).

(Continued)

*Primary Examiner* — Jessica Whiteley
(74) *Attorney, Agent, or Firm* — Myers Bigel, P.A.

(57) ABSTRACT

Disclosed herein are methods of forming a three-dimensional object having a biodegradable or bioerodible polymer or copolymer. In some embodiments, the methods include providing a dual cure resin with a photoinitiator, monomers and/or prepolymers that are polymerizable by exposure to actinic radiation or light, at least one cyclic ester, a ring-opening polymerization initiator, and a ring-opening polymerization catalyst. Resins useful for carrying out such methods, and products produced from such methods, are also described.

22 Claims, No Drawings

(56) References Cited

U.S. PATENT DOCUMENTS

| | | | |
|---|---|---|---|
| 9,211,678 B2 | 12/2015 | Desimone et al. | |
| 9,216,546 B2 | 12/2015 | Desimone et al. | |
| 9,360,757 B2 | 6/2016 | Desimone et al. | |
| 9,708,440 B2* | 7/2017 | Das | C08G 59/1477 |
| 9,777,097 B2 | 10/2017 | Liu et al. | |
| 2003/0091833 A1 | 5/2003 | Baumgart et al. | |
| 2004/0014832 A1 | 1/2004 | Baudin et al. | |
| 2004/0052966 A1 | 3/2004 | Wilke et al. | |
| 2004/0187714 A1 | 9/2004 | Napadensky | |
| 2007/0178133 A1 | 8/2007 | Rolland | |
| 2007/0205528 A1 | 9/2007 | Patel et al. | |
| 2008/0131692 A1 | 6/2008 | Rolland et al. | |
| 2010/0105794 A1 | 4/2010 | Dietliker et al. | |
| 2011/0151566 A1 | 6/2011 | Hedrick et al. | |
| 2012/0007287 A1 | 1/2012 | Vermeer et al. | |
| 2012/0195994 A1 | 8/2012 | El-Siblani et al. | |
| 2012/0251841 A1 | 10/2012 | Southwell et al. | |
| 2013/0292862 A1 | 11/2013 | Joyce | |
| 2013/0295215 A1 | 11/2013 | Wu et al. | |
| 2014/0256874 A1 | 9/2014 | Chasser et al. | |
| 2015/0215430 A1 | 7/2015 | Votour | |
| 2015/0322291 A1 | 11/2015 | Salviato et al. | |
| 2016/0136889 A1* | 5/2016 | Rolland | B29C 64/386 264/1.27 |
| 2017/0260418 A1 | 9/2017 | Wu et al. | |

FOREIGN PATENT DOCUMENTS

| | | |
|---|---|---|
| EP | 0562826 | 9/1993 |
| EP | 0442071 | 4/1997 |
| EP | 0830641 | 8/2003 |
| EP | 1341039 | 7/2008 |
| EP | 2224874 | 1/2014 |
| EP | 1918316 | 9/2015 |
| JP | H02111528 | 4/1990 |
| JP | H09194540 | 7/1997 |
| JP | 2000007641 | 1/2000 |
| WO | 92/07705 | 5/1992 |
| WO | 96/00412 | 1/1996 |
| WO | 2001/026023 | 4/2001 |
| WO | 2005/042630 | 5/2005 |
| WO | 2006/045002 | 4/2006 |
| WO | 2010/089264 | 8/2010 |
| WO | 2015/010924 | 1/2015 |
| WO | 2015/077419 | 5/2015 |
| WO | 2015/164234 | 10/2015 |

OTHER PUBLICATIONS

Malik et al. "A thermally reworkable UV curable acrylic adhesive prototype" International Journal of Adhesion & Adhesives, 22:283-289 (2002).

Malik et al. "Thermally Controlled Molecular Disassembly of a Crosslinked Polymer Network by the Incorporation of Sterically Hindered Urea Linkages" Journal of Applied Polymer Science, 85: 856-864 (2002).

Malik et al. "Computational study of thermally controlled polymer network disassembly via the incorporation of sterically hindered urea linkages" Polymer, 43: 2561-2567 (2002).

Malik et al. "The thermally controlled molecular disassembly properties of a polymer network via the incorporation of one sterically hindered urea linkage" Polymer Degradation and Stability, 76: 241-249 (2002).

Malik et al. "Comparative Study of Novel Polymer Prototype for Controlled Thermally Reworkable UV Curable Acrylic Adhesives in Absence and Presence of Reactive Diluent" Surface Engineering, 19(2): 121-126 (2003).

Park et al. "UV- and thermal-curing behaviors or dual-curable adhesives based on epoxy acrylate oligomers" International Journal of Adhesion and Adhesives, 29(7): 710-717 (2009).

Velankar et al. "High-performance UV-curable urethane acrylates via deblocking chemistry" Journal of Applied Polymer Science, 62(9):1361-1376 (1996).

Hall et al. "New developments in bond-forming initiation: Lewis acids accelerate spontaneous initiation of copolymerizations of olefins and dienes" Macromolecular Symposia, 95(1):233-242 (1995).

Pan et al. "A Fast Mask Projection Stereolithography Process for Fabricating Digital Models in Minutes" Journal of Manufacturing Science and Engineering, 134 (2012) 9 pp.

Tumbleston et al. "Continuous liquid interface production of 3D objects" Science, 347: 1349-1352 (2015).

Rydz et al. "Polyester-based (bio)degradable polymers as environmentally friendly materials for sustainable development" Int. J. Mol. Sci. 15:564-596 (2015).

Puls et al. "Degradation of cellulose acetate-base materials: a review" J. Polum. Environ., 19: 152-165 (2011).

Dove at al. "Thiourea-Based Bifunctional Organocatalysis:? Supramolecular Recognition for Living Polymerization" J. Am. Chem. Soc., 127(40):13798-13799 (2005). Abstract.

Lohmeijer et al. "Guanidine and Amidine Organocatalysts for Ring-Opening Polymerization of Cyclic Esters" Macromolecules, 39:8574-8583 (2006). Abstract.

Nuyken et al. "Ring-opening polymerization—an introductory review" Polymers, 5: 361-403 (2013).

Zhou et al. "Controlled ring-opening polymerization of cyclic esters with phosphoric acid as catalysts" Colloid Polym Sci., 291: 2155-2162 (2013).

* cited by examiner

CYCLIC ESTER DUAL CURE RESINS FOR ADDITIVE MANUFACTURING

RELATED APPLICATIONS

This application is a continuation of U.S. patent application Ser. No. 15/361,644, filed Nov. 28, 2016, which claims the benefit of U.S. Provisional Patent Application Ser. No. 62/270,646, filed Dec. 22, 2015, the disclosures of which are incorporated by reference herein in their entirety.

FIELD OF THE INVENTION

The present invention concerns materials, methods and apparatus for the fabrication of solid three-dimensional objects from liquid materials, and objects so produced.

BACKGROUND OF THE INVENTION

In conventional additive or three-dimensional fabrication techniques, construction of a three-dimensional object is performed in a step-wise or layer-by-layer manner. In particular, layer formation is performed through solidification of photo curable resin under the action of visible or UV light irradiation. Two techniques are known: one in which new layers are formed at the top surface of the growing object; the other in which new layers are formed at the bottom surface of the growing object. An early example is Hull, U.S. Pat. No. 5,236,637. Other approaches are shown in U.S. Pat. Nos. 7,438,846, 7,892,474, M. Joyce, US Patent App. 2013/0292862; Y. Chen et al., US Patent App. 2013/0295212 (both Nov. 7, 2013); Y. Pan et al., *J. Manufacturing Sci. and Eng.* 134, 051011-1 (October 2012), and numerous other references. Materials for use in such apparatus are generally limited, and there is a need for new resins to provide diverse material properties for different product families if three-dimensional fabrication is to achieve its full potential.

Southwell, Xu et al., US Patent Application Publication No. 2012/0251841, describe liquid radiation curable resins for additive fabrication, but these comprise a cationic photoinitiator (and hence are limited in the materials which may be used) and are suggested only for layer-by-layer fabrication. See also U.S. Pat. No. 8,980,971 to Ueda (DSM).

Velankar, Pazos, and Cooper, *Journal of Applied Polymer Science* 162, 1361 (1996), describe UV-curable urethane acrylates formed by a deblocking chemistry, but they are not suggested for additive manufacturing, and no suggestion is made on how those materials may be adapted to additive manufacturing.

SUMMARY OF THE INVENTION

A method of forming a three-dimensional object comprised of a biodegradable or bioerodible polymer or copolymer, is carried out by:

(a) providing a cyclic ester dual cure resin;

(b) forming a three-dimensional intermediate from the resin, where the intermediate has the shape of, or a shape to be imparted to, the three-dimensional object, and where the resin is solidified by exposure to light;

(c) optionally washing the three-dimensional intermediate, and then (d) heating and/or microwave irradiating the three-dimensional intermediate sufficiently to further cure the resin and form the three-dimensional object;

The cyclic ester dual cure resin comprises:
(i) a photoinitiator;
(ii) monomers and/or prepolymers that are polymerizable by exposure to actinic radiation or light;
(iii) optionally, a light absorbing pigment or dye;
(iv) at least one cyclic ester (e.g., 2 or 3 different cyclic esters);
(v) a ring-opening polymerization initiator;
(vi) a ring-opening polymerization catalyst;
(vii) optionally a diluent;
(viii) optionally a filler (e.g., an inert filler; a bioactive agent; combinations thereof).

Resins useful for carrying out such methods, and products produced from such methods, are also described.

In some embodiments, a Lewis acid or an oxidizable tin salt is included in the polymerizable liquid or resin (e.g., in an amount of from 0.01 or 0.1 to 1 or 2 percent by weight, or more) in an amount effective to accelerate the formation of the three-dimensional intermediate object during the production thereof.

In some embodiments of the methods and compositions described above and below, the polymerizable liquid (or "dual cure resin") has a viscosity of 100, 200, 500 or 1,000 centipoise or more at room temperature and/or under the operating conditions of the method, up to a viscosity of 10,000, 20,000, or 50,000 centipoise or more, at room temperature and/or under the operating conditions of the method.

In some embodiments, polymerizable liquids used in the present invention include a non-reactive pigment or dye. Examples include, but are not limited to, (i) titanium dioxide (e.g., in an amount of from 0.05 or 0.1 to 1 or 5 percent by weight), (ii) carbon black (e.g., included in an amount of from 0.05 or 0.1 to 1 or 5 percent by weight), and/or (iii) an organic ultraviolet light absorber such as a hydroxybenzophenone, hydroxyphenylbenzotriazole, oxanilide, benzophenone, hydroxypenyltriazine, thioxanthone, and/or benzotriazole ultraviolet light absorber (e.g. in an amount of 0.001 or 0.005 to 1, 2 or 4 percent by weight).

Non-limiting examples and specific embodiments of the present invention are explained in greater detail in the specification set forth below. The disclosures of all United States Patent references cited herein are to be incorporated herein by reference in their entirety.

DETAILED DESCRIPTION OF ILLUSTRATIVE EMBODIMENTS

The present invention is now described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete and will fully convey the scope of the invention to those skilled in the art.

As used herein, the term "and/or" includes any and all possible combinations or one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly-used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

"Shape to be imparted to" refers to the case where the shape of the intermediate object slightly changes between formation thereof and forming the subsequent three-dimensional product, typically by shrinkage (e.g., up to 1, 2 or 4 percent by volume), expansion (e.g., up to 1, 2 or 4 percent by volume), removal of support structures, or by intervening forming steps (e.g., intentional bending, stretching, drilling, grinding, cutting, polishing, or other intentional forming after formation of the intermediate product, but before formation of the subsequent three-dimensional product).

1. Resins.

As noted above, the present invention includes cyclic ester dual cure resin compositions useful for additive manufacturing. Such compositions comprise, consist of, or consist essentially of:

(i) a photoinitiator;

(ii) monomers and/or prepolymers that are polymerizable by exposure to actinic radiation or light;

(iii) optionally, a light absorbing pigment or dye;

(iv) at least one cyclic ester (e.g., 2 or 3 different cyclic esters);

(v) a ring-opening polymerization initiator;

(vi) a ring-opening polymerization catalyst;

(vii) optionally a diluent;

(viii) optionally a filler.

In some embodiments, the at least one cyclic ester is selected from the group consisting of lactides, lactones (including both six-membered ring lactones and seven-membered ring lactones), cyclic carbonates (including both five-membered ring cyclic carbonates and six-membered ring cyclic carbonates), and combinations thereof.

In some embodiments, the cyclic ester comprises a lactide of Formula Ia and/or Ib:

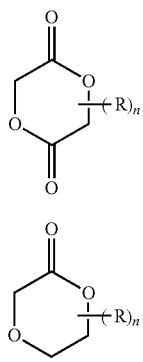

where each R is independently selected from H, hydroxyl, C1-C20 alkyl, C1-C20 allyl, C1-C20 alkoxy, C1-C26 arylalkyl, and C1-C26 arylalkoxy (e.g., benzyloxy); and n is 1, 2, or 3 (e.g., a lactide selected from the group consisting of 3,6-dimethyl-1,4-dioxane-2,5-dione (also referred to as "lactide"), 3-methyl-1,4-dioxane-2,5-dione, 1,4-dioxane-2,5-dione (also referred to as "glycolide"), p-dioxaneone, or a combination thereof).

In some embodiments, the cyclic ester comprises a lactone of Formula IIa and/or IIb:

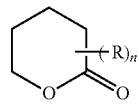

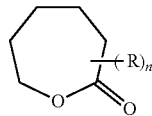

where each R is independently selected from H, hydroxyl, C1-C20 alkyl, C1-C20 allyl, C1-C20 alkoxy, C1-C26 arylalkyl, and C1-C26 arylalkoxy (e.g., benzyloxy); and n is 1, 2, 3 or 4 (e.g., a six-membered ring lactone selected from the group consisting of delta valerolactone, delta decalactone, delta dodecalactone, 5-decanolide, 5-dodecanolide, and delta hexalactone, or a seven membered ring lactone such as epsilon caprolactone, or a combination thereof).

In some embodiments, the cyclic ester comprises a cyclic carbonate of Formula IIIa and/or IIIb:

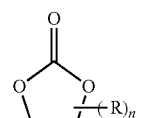

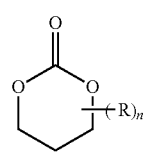

where each R is independently selected from H, hydroxyl, C1-C20 alkyl, C1-C20 allyl, C1-C20 alkoxy, C1-C26 arylalkyl, and C1-C26 arylalkoxy (e.g., benzyloxy); and n is 1, 2, or 3 (e.g., a five membered ring cyclic carbonate selected from the group consisting of ethylene carbonate, propylene carbonate, 4-ethyl-1,3-dioxolan-2-one; 4-vinyl-1,3,dioxolan-2-one, and 4-hydroxymethyl-1,3-dioxolane-2-one; or a six-membered ring cyclic carbonate selected from the group consisting of 1,3-dioxane-2-one, 5,5-diethyl-1,3-dioxane-2-one, 5-methyl-5-propyl-1,3-dioxane-2-one, 5-(benzyloxy)-1,3-dioxan-2-one, 5,5-dimethoxy-1,3-dioxan-2-one, 5-hydroxy-1-3,dioxan-2-one, 1,3-dioxan-2,5-dione, or a combination thereof).

In some embodiments, the initiator is selected from the group consisting of alcohols (e.g., primary alcohols and polyols including diols), trialkyl borates such as tributyl borate, trialkoxy borates such as triethanolamine borate, and tris(trimethylsilyl) borate.

In some embodiments, the catalyst is selected from the group consisting of Tin(II) octoate, metal carboxylates, metal acetylacetonate (e.g., Li, Mg, Zr, Zn, Ca, Fe), dibutyl tin(IV) dilaurate, organophosphoric acids, basic organocatalysts, tertiary amines (e.g., 4-(dimethylamino)pyridine), phosphines, and N-heterocyclic carbenes (NHCs). There is also a catalyst pair based on bifunctional organocatalysis, using thiourea-tertiary amines (see generally Dove, A. P.; Pratt, R. C.; Lohmeijer, B. G. G.; Waymouth, R. M.; Hedrick, J. L. *J. Am. Chem. Soc.* 2005, 127 13798-13799).

The catalyst can be chosen based on the type of initiator used. For example, a relatively strong organic acid (such as toluenesulfonic acid, fluoronated alkyl sulfonic acid) is preferably used as a catalyst when trialkyl borate is the initiator, whereas tertiary amines, organophosphoric acids and metal carboxlyates (or acetyl acetonate) are preferably used as the catalyst when an alcohol is the initiator.

In some embodiments, the monomers and/or prepolymers polymerizable by exposure to actinic radiation or light comprise reactive end groups selected from the group consisting of acrylates, methacrylates, α-olefins, N-vinyls, acrylamides, methacrylamides, styrenics, epoxides, thiols, 1,3-dienes, vinyl halides, acrylonitriles, vinyl esters, maleimides, and vinyl ethers. (See, e.g., US Patent Application Publication No. 2015/0072293 to DeSimone et al).

Any suitable filler may be used in connection with the present invention, depending on the properties desired in the part or object to be made. Thus, fillers may be solid or liquid, organic or inorganic, and may include reactive and non-reactive rubbers: siloxanes, acrylonitrile-butadiene rubbers; reactive and non-reactive thermoplastics (including but not limited to: poly(ether imides), maleimide-styrene terpolymers, polyarylates, polysulfones and polyethersulfones, etc.) inorganic fillers such as silicates (such as talc, clays, silica, mica), glass, carbon nanotubes, graphene, cellulose nanocrystals, etc., including combinations of all of the foregoing.

In some embodiments, the light absorbing pigment or dye is:

(i) titanium dioxide (e.g., in an amount of from 0.05 or 0.1 to 1 or 5 percent by weight), (ii) carbon black (e.g., in an amount of from 0.05 or 0.1 to 1 or 5 percent by weight), and/or (iii) an organic ultraviolet light absorber (e.g., a hydroxybenzophenone, hydroxyphenylbenzotriazole, oxanilide, benzophenone, thioxanthone, hydroxyphenyltriazine, and/or benzotriazole ultraviolet light absorber) (e.g., in an amount of 0.001 or 0.005 to 1 or 2 percent by weight).

In some embodiments, the diluent comprises an acrylate, a methacrylate, a styrene, an acrylic acid, a vinylamide, a vinyl ether, a vinyl ester, polymers containing any one or more of the foregoing, and combinations of two or more of the foregoing.

In some embodiments of the foregoing, the polymerizable liquid comprises:

(i) from 0.1 to 4 percent by weight of the photoinitiator;

(ii) from 10 to 40, 60, or 90 percent by weight of the monomers and/or prepolymers that are polymerizable by exposure to actinic radiation or light;

(iii) from 0.001 to 5 percent by weight of the light absorbing pigment or dye when present;

(iv) from 10, 20, 40 or 50 to 60, 80 or 90 percent by weight of the at least one cyclic ester;

(v) from 0.001, 0.01 or 0.1 to 2, 4, 6 or 8 percent by weight of the ring-opening polymerization initiator;

(vi) from 0.001, 0.01, or 0.1 to 2, 4, 6 or 8 percent by weight of the ring-opening polymerization catalyst;

(vii) from 1 to 40 percent by weight of said diluent when present; and (viii) from 1 to 50 percent by weight of said filler when present.

In some embodiments, the polymerizable liquid may contain a degredation enhancer, such as when a more rapid rate of biodegradation or bioerosion is desired. See, e.g., J. Rydz et al., *Polyester-based (bio) degradable polymers as environmentally friendly materials for sustainable development*, Int. J. Mol. Sci. 16, 564-596 (2015); J. Puls et al., *Degradation of cellulose acetate-based materials*: A review, J. Polym. Environ. 19: 152-165 (2011).

In some embodiments, a Lewis acid or an oxidizable tin salt is included in the polymerizable liquid (e.g., in an amount of from 0.01 or 0.1 to 1 or 2 percent by weight, or more) in an amount effective to accelerate the formation of the three-dimensional intermediate object during the production thereof. Oxidizable tin salts useful for carrying out the present invention include, but are not limited to, stannous butanoate, stannous octoate, stannous hexanoate, stannous heptanoate, stannous linoleate, stannous phenyl butanoate, stannous phenyl stearate, stannous phenyl oleate, stannous nonanoate, stannous decanoate, stannous undecanoate, stannous dodecanoate, stannous stearate, stannous oleate stannous undecenoate, stannous 2-ethylhexoate, dibutyl tin dilaurate, dibutyl tin dioleate, dibutyl tin distearate, dipropyl tin dilaurate, dipropyl tin dioleate, dipropyl tin distearate, dibutyl tin dihexanoate, and combinations thereof. See also U.S. Pat. Nos. 5,298,532; 4,421,822; and 4,389,514, the disclosures of which are incorporated herein by reference. In addition to the foregoing oxidizable tin salts, Lewis acids such as those described in Chu et al. in Macromolecular Symposia, Volume 95, Issue 1, pages 233-242, June 1995 are known to enhance the polymerization rates of free-radical polymerizations and are included herein by reference.

Any suitable filler may be used in connection with the present invention, depending on the properties desired in the part or object to be made. Thus, fillers may be solid or liquid, organic or inorganic, and may include reactive and non-reactive rubbers: siloxanes, acrylonitrile-butadiene rubbers; reactive and non-reactive thermoplastics (including but not limited to: poly(ether imides), maleimide-styrene terpolymers, polyarylates, polysulfones and polyethersulfones, etc.) inorganic fillers such as silicates (such as talc, clays, silica, mica), glass, carbon nanotubes, graphene, cellulose nanocrystals, etc., including combinations of all of the foregoing. Suitable fillers include tougheners, such as core-shell rubbers, as discussed below.

Tougheners.

One or more polymeric and/or inorganic tougheners can be used as a filler in the present invention. See generally US Patent Application Publication No. 20150215430. The toughener may be uniformly distributed in the form of particles in the cured product. The particles could be less than 5 microns (μm) in diameter. Such tougheners include, but are not limited to, those formed from elastomers, branched polymers, hyperbranched polymers, dendrimers, rubbery polymers, rubbery copolymers, block copolymers, core-shell particles, oxides or inorganic materials such as clay, polyhedral oligomeric silsesquioxanes (POSS), carbonaceous materials (e.g., carbon black, carbon nanotubes, carbon nanofibers, fullerenes), ceramics and silicon carbides, with or without surface modification or functionalization. Examples of block copolymers include the copolymers whose composition is described in U.S. Pat. No. 6,894,113 (Court et al., Atofina, 2005) and include "NANOSTRENTH®" SBM (polystyrene-polybutadiene-polymethacrylate), and AMA (polymethacrylate-polybutylacrylate-polymethacrylate), both produced by Arkema. Other suitable block copolymers include FORTEGRA™ and the amphiphilic block copolymers described in U.S. Pat. No. 7,820,760B2, assigned to Dow Chemical. Examples of known core-shell particles include the core-shell (dendrimer) particles whose compositions are described in US20100280151A1 (Nguyen et al., Toray Industries, Inc., 2010) for an amine branched polymer as a shell grafted to a core polymer polymerized from polymerizable monomers containing unsaturated carbon-carbon bonds, core-shell rubber particles whose compositions are described in EP 1632533A1 and EP 2123711A1 by Kaneka Corporation, and the "KaneAce MX" product line of such particle/epoxy blends whose particles have a polymeric core polymerized from polymerizable monomers such as butadiene, styrene, other unsaturated carbon-carbon bond monomer, or their combinations, and a polymeric shell compatible with the epoxy, typically polymethylmethacrylate, polyglycidylmethacrylate, polyacrylonitrile or similar polymers, as discussed further below. Also suitable as block copolymers in the present invention are the "JSR SX" series of carboxylated polystyrene/polydivinylbenzenes produced by JSR Corporation; "Kureha Paraloid" EXL-2655 (produced by Kureha Chemical Industry Co., Ltd.), which is a butadiene alkyl methacrylate styrene copolymer; "Stafiloid" AC-3355 and TR-2122 (both produced by Takeda Chemical Industries, Ltd.), each of which are acrylate methacrylate copolymers; and "PARALOID" EXL-2611 and EXL-3387 (both produced by Rohm & Haas), each of which are butyl acrylate methyl methacrylate copolymers. Examples of suitable oxide particles include NANOPDX® produced by nanoresins AG. This is a master blend of functionalized nanosilica particles and an epoxy.

Core-Shell Rubbers.

Core-shell rubbers are particulate materials (particles) having a rubbery core. Such materials are known and described in, for example, US Patent Application Publication No. 20150184039, as well as US Patent Application Publication No. 20150240113, and U.S. Pat. Nos. 6,861,475, 7,625,977, 7,642,316, 8,088,245, and elsewhere.

In some embodiments, the core-shell rubber particles are nanoparticles (i.e., having an average particle size of less than 1000 nanometers (nm)). Generally, the average particle size of the core-shell rubber nanoparticles is less than 500 nm, e.g., less than 300 nm, less than 200 nm, less than 100 nm, or even less than 50 nm. Typically, such particles are spherical, so the particle size is the diameter; however, if the particles are not spherical, the particle size is defined as the longest dimension of the particle.

In some embodiments, the rubbery core can have a glass transition temperature (Tg) of less than −25° C., more preferably less than −50° C., and even more preferably less than −70° C. The Tg of the rubbery core may be well below −100° C. The core-shell rubber also has at least one shell portion that preferably has a Tg of at least 50° C. By "core," it is meant an internal portion of the core-shell rubber. The core may form the center of the core-shell particle, or an internal shell or domain of the core-shell rubber. A shell is a portion of the core-shell rubber that is exterior to the rubbery core. The shell portion (or portions) typically forms the outermost portion of the core-shell rubber particle. The shell material can be grafted onto the core or is cross-linked. The rubbery core may constitute from 50 to 95%, or from 60 to 90%, of the weight of the core-shell rubber particle.

The core of the core-shell rubber may be a polymer or copolymer of a conjugated diene such as butadiene, or a lower alkyl acrylate such as n-butyl-, ethyl-, isobutyl- or 2-ethylhexylacrylate. The core polymer may in addition contain up to 20% by weight of other copolymerized monounsaturated monomers such as styrene, vinyl acetate, vinyl chloride, methyl methacrylate, and the like. The core polymer is optionally cross-linked. The core polymer optionally contains up to 5% of a copolymerized graft-linking monomer having two or more sites of unsaturation of unequal reactivity, such as diallyl maleate, monoallyl fumarate, allyl methacrylate, and the like, at least one of the reactive sites being non-conjugated.

The core polymer may also be a silicone rubber. These materials often have glass transition temperatures below −100° C. Core-shell rubbers having a silicone rubber core include those commercially available from Wacker Chemie, Munich, Germany, under the trade name Genioperl®.

The shell polymer, which is optionally chemically grafted or cross-linked to the rubber core, can be polymerized from at least one lower alkyl methacrylate such as methyl methacrylate, ethyl methacrylate or t-butyl methacrylate. Homopolymers of such methacrylate monomers can be used. Further, up to 40% by weight of the shell polymer can be formed from other monovinylidene monomers such as styrene, vinyl acetate, vinyl chloride, methyl acrylate, ethyl acrylate, butyl acrylate, and the like. The molecular weight of the grafted shell polymer can be between 20,000 and 500,000.

One suitable type of core-shell rubber has reactive groups in the shell polymer which can react with an epoxy resin or an epoxy resin hardener. Glycidyl groups are suitable. These can be provided by monomers such as glycidyl methacrylate.

One example of a suitable core-shell rubber is of the type described in US Patent Application Publication No. 2007/0027233 (EP 1 632 533 A1). Core-shell rubber particles as described therein include a cross-linked rubber core, in most cases being a cross-linked copolymer of butadiene, and a shell which is preferably a copolymer of styrene, methyl methacrylate, glycidyl methacrylate and optionally acrylonitrile. The core-shell rubber is preferably dispersed in a polymer or an epoxy resin, also as described in the document.

Suitable core-shell rubbers include, but are not limited to, those sold by Kaneka Corporation under the designation Kaneka Kane Ace, including the Kaneka Kane Ace 15 and 120 series of products, including Kaneka Kane Ace MX 120, Kaneka Kane Ace MX 153, Kaneka Kane Ace MX 154, Kaneka Kane Ace MX 156, Kaneka Kane Ace MX170, and Kaneka Kane Ace MX 257 and Kaneka Kane Ace MX 120 core-shell rubber dispersions, and mixtures thereof.

2. Methods.

The three-dimensional intermediate is preferably formed from resins as described above by additive manufacturing, typically bottom-up or top-down additive manufacturing. Such methods are known and described in, for example, U.S. Pat. No. 5,236,637 to Hull, U.S. Pat. Nos. 5,391,072 and 5,529,473 to Lawton, U.S. Pat. No. 7,438,846 to John, U.S. Pat. No. 7,892,474 to Shkolnik, U.S. Pat. No. 8,110,135 to El-Siblani, U.S. Patent Application Publication Nos. 2013/0292862 to Joyce and 2013/0295212 to Chen et al., and PCT Application Publication No. WO 2015/164234 to Robeson et al. The disclosures of these patents and applications are incorporated by reference herein in their entirety.

In general, top-down three-dimensional fabrication is carried out by:

(a) providing a polymerizable liquid reservoir having a polymerizable liquid fill level and a carrier positioned in the reservoir, the carrier and the fill level defining a build region therebetween;

(b) filling the build region with a polymerizable liquid (i.e., the resin), said polymerizable liquid comprising a mixture of (i) a light (typically ultraviolet light) polymerizable liquid first component, and (ii) a second solidifiable component of the dual cure system; and then (c) irradiating the build region with light to form a solid polymer scaffold from the first component and also advancing (typically lowering) the carrier away from the build surface to form a three-dimensional intermediate having the same shape as, or a shape to be imparted to, the three-dimensional object and containing said second solidifiable component (e.g., a second reactive component) carried in the scaffold in unsolidified and/or uncured form.

A wiper blade, doctor blade, or optically transparent (rigid or flexible) window, may optionally be provided at the fill level to facilitate leveling of the polymerizable liquid, in accordance with known techniques. In the case of an optically transparent window, the window provides a build surface against which the three-dimensional intermediate is formed, analogous to the build surface in bottom-up three-dimensional fabrication as discussed below.

In general, bottom-up three-dimensional fabrication is carried out by:

(a) providing a carrier and an optically transparent member having a build surface, the carrier and the build surface defining a build region therebetween;

(b) filling the build region with a polymerizable liquid (i.e., the resin), said polymerizable liquid comprising a mixture of (i) a light (typically ultraviolet light) polymerizable liquid first component, and (ii) a second solidifiable component of the dual cure system; and then (c) irradiating the build region with light through said optically transparent member to form a solid polymer scaffold from the first component and also advancing (typically raising) the carrier away from the build surface to form a three-dimensional intermediate having the same shape as, or a shape to be imparted to, the three-dimensional object and containing said second solidifiable component (e.g., a second reactive component) carried in the scaffold in unsolidified and/or uncured form.

In some embodiments of bottom-up or top-down three-dimensional fabrication as implemented in the context of the present invention, the build surface is stationary during the formation of the three-dimensional intermediate; in other embodiments of bottom-up three-dimensional fabrication as implemented in the context of the present invention, the build surface is tilted, slid, flexed and/or peeled, and/or otherwise translocated or released from the growing three-dimensional intermediate, usually repeatedly, during formation of the three-dimensional intermediate.

In some embodiments of bottom-up or top-down three-dimensional fabrication as carried out in the context of the present invention, the polymerizable liquid (or resin) is maintained in liquid contact with both the growing three dimensional intermediate and the build surface during both the filling and irradiating steps, during fabrication of some of, a major portion of, or all of the three-dimensional intermediate.

In some embodiments of bottom-up or top-down three-dimensional fabrication as carried out in the context of the present invention, the growing three-dimensional intermediate is fabricated in a layerless manner (e.g., through multiple exposures or "slices" of patterned actinic radiation or light) during at least a portion of the formation of the three-dimensional intermediate.

In some embodiments of bottom-up or top-down three-dimensional fabrication as carried out in the context of the present invention, the growing three-dimensional intermediate is fabricated in a layer-by-layer manner (e.g., through multiple exposures or "slices" of patterned actinic radiation or light), during at least a portion of the formation of the three-dimensional intermediate.

In some embodiments of bottom-up or top-down three-dimensional fabrication employing a rigid or flexible optically transparent window, a lubricant or immiscible liquid may be provided between the window and the polymerizable liquid (e.g., a fluorinated fluid or oil such as a perfluoropolyether oil).

From the foregoing it will be appreciated that, in some embodiments of bottom-up or top-down three-dimensional fabrication as carried out in the context of the present invention, the growing three-dimensional intermediate is fabricated in a layerless manner during the formation of at least one portion thereof, and that same growing three-dimensional intermediate is fabricated in a layer-by-layer manner during the formation of at least one other portion thereof. Thus, operating mode may be changed once, or on multiple occasions, between layerless fabrication and layer-by-layer fabrication, as desired by operating conditions such as part geometry.

In preferred embodiments, the intermediate is formed by continuous liquid interface production (CLIP). CLIP is known and described in, for example, PCT Application Nos. PCT/US2014/015486 (published as U.S. Pat. No. 9,211,678 on Dec. 15, 2015); PCT/US2014/015506 (also published as U.S. Pat. No. 9,205,601 on Dec. 8, 2015), PCT/US2014/015497 (also published as US 2015/0097316, and as U.S. Pat. No. 9,216,546 on Dec. 22, 2015), and in J. Tumbleston, D. Shirvanyants, N. Ermoshkin et al., Continuous liquid interface production of 3D Objects, *Science* 347, 1349-1352 (published online 16 Mar. 2015). In some embodiments, CLIP employs features of a bottom-up three-dimensional fabrication as described above, but the irradiating and/or said advancing steps are carried out while also concurrently maintaining a stable or persistent liquid interface between the growing object and the build surface or window, such as by: (i) continuously maintaining a dead zone of polymerizable liquid in contact with said build surface, and (ii) continuously maintaining a gradient of polymerization zone (such as an active surface) between the dead zone and the solid polymer and in contact with each thereof, the gradient of polymerization zone comprising the first component in partially cured form. In some embodiments of CLIP, the optically transparent member comprises a semipermeable member (e.g., a fluoropolymer), and the continuously maintaining a dead zone is carried out by feeding an inhibitor of polymerization through the optically transparent member, thereby creating a gradient of inhibitor in the dead zone and optionally in at least a portion of the gradient of polymerization zone.

In some embodiments, the stable liquid interface may be achieved by other techniques, such as by providing an immiscible liquid as the build surface between the polymerizable liquid and the optically transparent member, by feeding a lubricant to the build surface (e.g., through an optically transparent member which is semipermeable thereto, and/or serves as a reservoir thereof), etc.

While the dead zone and the gradient of polymerization zone do not have a strict boundary therebetween (in those locations where the two meet), the thickness of the gradient of polymerization zone is in some embodiments at least as great as the thickness of the dead zone. Thus, in some embodiments, the dead zone has a thickness of from 0.01, 0.1, 1, 2, or 10 microns up to 100, 200 or 400 microns, or more, and/or the gradient of polymerization zone and the dead zone together have a thickness of from 1 or 2 microns up to 400, 600, or 1000 microns, or more. Thus the gradient of polymerization zone may be thick or thin depending on the particular process conditions at that time. Where the gradient of polymerization zone is thin, it may also be described as an active surface on the bottom of the growing three-dimensional object, with which monomers can react and continue to form growing polymer chains therewith. In some embodiments, the gradient of polymerization zone, or active surface, is maintained (while polymerizing steps continue) for a time of at least 5, 10, 15, 20 or 30 seconds, up to 5, 10, 15 or 20 minutes or more, or until completion of the three-dimensional product.

Inhibitors, or polymerization inhibitors, for use in the present invention may be in the form of a liquid or a gas. In some embodiments, gas inhibitors are preferred. In some embodiments, liquid inhibitors such as oils or lubricants may be employed. In further embodiments, gas inhibitors which are dissolved in liquids (e.g. oils or lubricants) may be employed, for example, oxygen dissolved in a fluorinated fluid. The specific inhibitor will depend upon the monomer being polymerized and the polymerization reaction. For free radical polymerization monomers, the inhibitor can conveniently be oxygen, which can be provided in the form of a gas such as air, a gas enriched in oxygen (optionally but in some embodiments preferably containing additional inert gases to reduce combustibility thereof), or in some embodiments pure oxygen gas. In alternate embodiments, such as where the monomer is polymerized by photoacid generator initiator, the inhibitor can be a base such as ammonia, trace amines (e.g. methyl amine, ethyl amine, di and trialkyl amines such as dimethyl amine, diethyl amine, trimethyl amine, triethyl amine, etc.), or carbon dioxide, including mixtures or combinations thereof.

The method may further comprise the step of disrupting the gradient of polymerization zone for a time sufficient to form a cleavage line in the three-dimensional object (e.g., at a predetermined desired location for intentional cleavage, or at a location in the object where prevention of cleavage or reduction of cleavage is non-critical), and then reinstating the gradient of polymerization zone (e.g. by pausing, and resuming, the advancing step, increasing, then decreasing, the intensity of irradiation, and combinations thereof).

CLIP may be carried out in different operating modes (that is, different manners of advancing the carrier and build surface away from one another), including continuous, intermittent, reciprocal, and combinations thereof.

Thus in some embodiments, the advancing step is carried out continuously, at a uniform or variable rate, with either constant or intermittent illumination or exposure of the build area to the light source.

In other embodiments, the advancing step is carried out sequentially in uniform increments (e.g., of from 0.1 or 1 microns, up to 10 or 100 microns, or more) for each step or increment. In some embodiments, the advancing step is carried out sequentially in variable increments (e.g., each increment ranging from 0.1 or 1 microns, up to 10 or 100 microns, or more) for each step or increment. The size of the increment, along with the rate of advancing, will depend in part upon factors such as temperature, pressure, structure of the article being produced (e.g., size, density, complexity, configuration, etc.).

In some embodiments, the rate of advance (whether carried out sequentially or continuously) is from about 0.1 1, or 10 microns per second, up to about to 100, 1,000, or 10,000 microns per second, again depending again depending on factors such as temperature, pressure, structure of the article being produced, intensity of radiation, etc.

In still other embodiments, the carrier is vertically reciprocated with respect to the build surface to enhance or speed the refilling of the build region with the polymerizable liquid. In some embodiments, the vertically reciprocating step, which comprises an upstroke and a downstroke, is carried out with the distance of travel of the upstroke being greater than the distance of travel of the downstroke, to thereby concurrently carry out the advancing step (that is, driving the carrier away from the build plate in the Z dimension) in part or in whole.

In some embodiments, the solidifiable or polymerizable liquid is changed at least once during the method with a subsequent solidifiable or polymerizable liquid (e.g., by switching a "window" or "build surface" and associated reservoir of polymerizable liquid in the apparatus); optionally where the subsequent solidifiable or polymerizable liquid is cross-reactive with each previous solidifiable or polymerizable liquid during the subsequent curing, to form an object having a plurality of structural segments covalently coupled to one another, each structural segment having different structural (e.g., tensile) properties (e.g., a rigid funnel or liquid connector segment, covalently coupled to a flexible pipe or tube segment).

Once the three-dimensional intermediate is formed, it may be removed from the carrier, optionally washed, any supports optionally removed, any other modifications optionally made (cutting, welding, adhesively bonding, joining, grinding, drilling, etc.), and then heated and/or microwave irradiated sufficiently to further cure the resin and form the three-dimensional object. Of course, additional modifications may also be made following the heating and/or microwave irradiating step.

Washing may be carried out with any suitable organic or aqueous wash liquid, or combination thereof, including solutions, suspensions, emulsions, microemulsions, etc. Examples of suitable wash liquids include, but are not limited to water, alcohols (e.g., methanol, ethanol, isopropanol, etc.), benzene, toluene, etc. Such wash solutions may optionally contain additional constituents such as surfactants, etc. A currently preferred wash liquid is a 50:50 (volume:volume) solution of water and isopropanol. Wash methods such as those described in U.S. Pat. No. 5,248,456 may be employed and are included herein.

After the intermediate is formed, optionally washed, etc., as described above, it is then heated and/or microwave irradiated to further cure the same. Heating may be active heating (e.g., in an oven, such as an electric, gas, or solar oven), or passive heating (e.g., at ambient temperature). Active heating will generally be more rapid than passive heating and in some embodiments is preferred, but passive heating—such as simply maintaining the intermediate at ambient (room) temperature for a sufficient time to effect further cure—is in some embodiments preferred.

In some embodiments, the heating step is carried out at at least a first (oven) temperature and a second (oven) temperature, with the first temperature greater than ambient temperature, the second temperature greater than the first temperature, and the second temperature less than 300° C.

(e.g., with ramped or step-wise increases between ambient temperature and the first temperature, and/or between the first temperature and the second temperature).

For example, the intermediate may be heated in a stepwise manner at a first temperature of about 70° C. to about 150° C., and then at a second temperature of about 150° C. to 200 or 250° C., with the duration of each heating depending on the size, shape, and/or thickness of the intermediate. In another embodiment, the intermediate may be cured by a ramped heating schedule, with the temperature ramped from ambient temperature through a temperature of 70 to 150° C., and up to a final (oven) temperature of 250 or 300° C., at a change in heating rate of 0.5° C. per minute, to 5° C. per minute. (See, e.g., U.S. Pat. No. 4,785,075).

It will be clear to those skilled in the art that the materials described in the current invention will be useful in other additive manufacturing techniques, including ink jet printer-based methods.

3. Products.

The resins and methods described above are particularly useful for making three-dimensional objects or products that are biodegradable, bioerodable, and/or implantable.

Where a combination of different cyclic esters is used in the resin, the resulting object or product may be comprised of a copolymer, examples of which include but are not limited to: poly(1-lactide-co-glycolide) (PLG) (also referred to as poly(lactic-co-glycolic acid) or PLGA); poly(1-lactide-co-epsilon-caprolactone) (PLLC or PLCL); and poly(1-lactide-co-glycolide-co-epsilon-caprolactone) (PLGC).

Consumer products, such as children's toys, containers, and packaging materials, that might otherwise persist in the environment upon being discarded, can be made from polymerizable liquids and methods of the present invention.

Examples of biomedical implants include, but are not limited to, vascular devices (stents, inferior vena cava filters, septal defect closure devices, etc.) orthopedic devices (screws, plates, rods, spinal cages, etc.), therapeutic drug delivery depots or devices (e.g., microneedle arrays, ocular implants, etc.), including combination products relying on polymer erosion to deliver therapeutics.

Bioactive Agents.

In some embodiments, particularly those products intended for implant into a human or animal subject, the filler may be a bioactive agent or therapeutic compound (or combination thereof), such as an agent from the group of pharmacologically active antibiotic drugs, antiviral drugs, neoplastic agents, steroids, fibronectin, anti-clotting drugs, anti-platelet function drugs, drugs which prevent smooth muscle cell growth on inner surface wall of vessel, bioactive agents, the therapeutic agent may comprise proteins, peptides, anti-inflammatory agents, antibiotic agent, antiproliferative agents, drugs, anticoagulant agents, free radical scavengers, steroidal anti-inflammatory agents, antibiotics, nitric oxide donors, super oxide dismutases, super oxide dismutases mimics, cytostatic agents, prodrugs thereof, co-drugs thereof, or combinations thereof. Particular examples of bioactive agents include, but are not limited to, heparin, heparin fragments, aspirin, coumadin, tissue plasminogen activator, urokinase, hirudin, streptokinase, antiproliferative agents, antioxidants, antimetabolites, thromboxane inhibitors, non-steroidal and steroidal anti-inflammatory drugs, immunosuppressents, beta and calcium channel blockers, genetic materials including DNA and RNA fragments, complete expression genes, antibodies, lymphokines, growth factors, vascular endothelial growth factor, fibroblast growth factor, prostaglandins, leukotrienes, laminin, elastin, collagen, nitric oxide, integrins, paclitaxel, taxol, rapamycin, rapamycin derivatives and analogues, sirolimus, rapamune, tacrolimus, dexamethasone, everolimus, ABT-578, growth factors, zotarolimus, dexamethasone, clobetasol, estradiol, 4-amino-2,2,6,6-tetramethylpiperidine-1-oxyl (4-amino-TEMPO), 4-hydroxy-2,2,6,6-tetramethylpiperidine-1-oxyl (TEMPOL), 40-O-(3-hydroxy)propyl-rapamycin, 40-O-[2-(2-hydroxy)ethoxy]ethyl-rapamycin, and 40-O-tetrazole-rapamycin, including prodrugs thereof and combinations thereof (see, e.g., US Patent Application Publication No. 20150342761; see also US Patent Application Publication No. 20140147485).

Embodiments of the present invention are explained in greater detail in the following non-limiting examples.

Examples 1-4

Conventionally, UV curable bioabsorbable materials are based on di-methacrylate/acrylate terminated crosslinkers with bioabsorbable oligomers as the linkage. Such linkage may be polyethylene glycol (PEG), polylactic acid (PLA), polyglycolic acid (PGA), polycaprolactone (PCL), polydioxanone (PDO), poly(4-hydroxybutyrate) (P4HB), and their copolymers. Although this approach works in producing UV curable bioabsorbable materials, the resulting material can have a high fraction of methacrylate/acrylate backbone which is generally considered non-bioabsorbable. Upon complete degradation of the bioabsorbable linkages, carboxylic acid groups are produced on methacrylate/acrylate backbone, making it soluble in aqueous environment. However, if the molecular weight of methacrylic/acrylic acid is higher than 30,000, the backbone becomes difficult to dissolve in an aqueous environment.

An orthogonal curing system can potentially mitigate these issues. In addition to the UV curable network, there is a secondary thermally-induced polymerization that produces bioabsorbable polymers. This formulation comprises two categories of components: (i) light (e.g., UV light) curable components and (ii) monomeric/or oligomeric bioabsorbable components. The UV curable components are used to define part shape and provide necessary mechanical strength during initial production of the intermediate. The monomeric bioabsorbable components undergo ring-opening polymerization at elevated temperatures to form linear or crosslinked pure bioabsorbable polymer.

The UV curable portion in this dual cure formulation typically comprises a photoinitiator (preferably biocompatible considering the end application of such dual cure resins), bioabsorbable crosslinkers (mentioned in the first paragraph), and optional bioabsorbale monomers (used as a diluent)

The secondary curing is preferably by ring-opening polymerization. This portion of formulation consists of an initiator, a catalyst and a monomer(s). An illustrative example is the ring opening polymerization of epsilon-caprolactone.

A common initiator is an alcohol (e.g., primary alcohol, diol, polyol) or a trialkyl borate. Catalyst is chosen based on the type of initiator. All of these catalysts facilitate the nucleophilic substitution on the lactone carbonyl group. Examples are given below.

Example 1

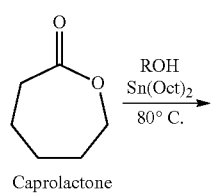

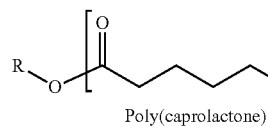

An alcohol is used as the initiator. The ring-opening polymerization is catalyzed by Tin(II) Octoate at elevated temperatures (>60° C.). The reason for curing above 60° C. is that polycaprolactone is crystalline and melts slightly below 60° C. To obtain a significant polymerization rate, the product must be in liquid state.

Example 2

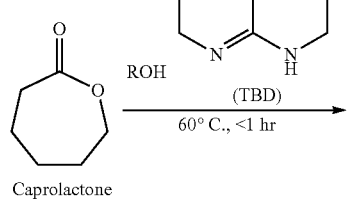

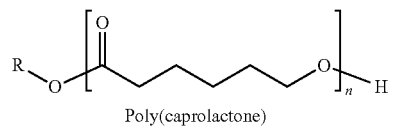

An alcohol is used as the initiator. The ring-opening polymerization is catalyzed by a basic organocatalyst, commonly 1,5,7-Triazabicyclo[4.4.0]dec-5-ene (TBD), N-methyl-TBD (MTBD), and 1,8-diazabicyclo[5.4.0]-undec-7-ene (DBU). TBD was shown to be most effective in catalyzing ring-opening polymerization of caprolactone. See Lohmeijer et al., "Guanidine and Amidine Organocatalysts for Ring-opening Polymerization of Cyclic Esters," *Macromolecules* 2006, 39, 8574-8583.

Example 3

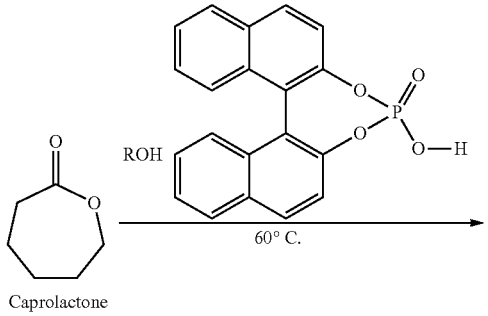

This Example is similar to Example 2. The difference is that instead of being catalyzed by a basic organocatalyst, the ring-opening polymerization is catalyzed by an organophosphoric acid, (R)-(−)-1,1′-Binaphthyl-2,2′-diyl hydrogen phosphate (BPA). See Zhou et al., "Controlled Ring-opening Polymerization of Cyclic Esters with Phosphoric Acid as Catalysts," *Colloid Polm. Sci.* 2013, 291, 2155-2162.

Example 4

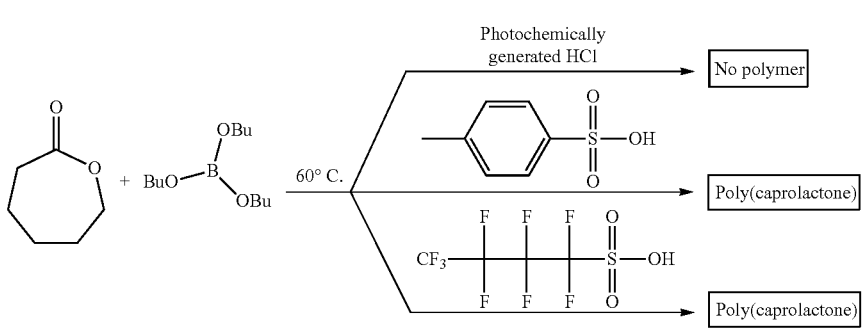

Tributyl borate is used as the initiator. The ring-opening polymerization propagates from the borate center, forming a three-arm star-branched polycaprolactone. The polymerization can be catalyzed by acids with various degree of acidity. Latent acids that can be released from photoacid generators are advantageously employed. That way, we can produce acid when it is needed using light to prevent dark polymerization at room temperature due to the presence of the acid.

The foregoing is illustrative of the present invention, and is not to be construed as limiting thereof. The invention is defined by the following claims, with equivalents of the claims to be included therein.

We claim:

1. A method of forming a three-dimensional object comprised of a biodegradable or bioerodible polymer or copolymer, the method comprising:
    (a) providing a cyclic ester dual cure resin;
    (b) forming a three-dimensional intermediate from said resin, where said intermediate has the shape of, or a shape to be imparted to, said three-dimensional object, and where said resin is solidified by exposure to light;
    (c) optionally washing the three-dimensional intermediate, and then
    (d) heating and/or microwave irradiating said three-dimensional intermediate sufficiently to further cure said resin and form said three-dimensional object;
  wherein said cyclic ester dual cure resin comprises:
    (i) a photoinitiator;
    (ii) monomers and/or prepolymers that are polymerizable by exposure to actinic radiation or light;
    (iii) optionally, a light absorbing pigment or dye;
    (iv) at least one cyclic ester;
    (v) a ring-opening polymerization initiator;
    (vi) a ring-opening polymerization catalyst;
    (vii) optionally a diluent; and
    (viii) optionally a filler.

2. The method of claim 1, wherein said at least one cyclic ester is selected from the group consisting of lactides, lactones, cyclic carbonates, and combinations thereof.

3. The method of claim 1, wherein said at least one cyclic ester comprises a lactide of Formula Ia and/or Ib:

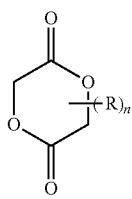

(Ia)

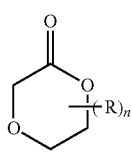

(Ib)

wherein each R is independently selected from H, hydroxyl, C1-C20 alkyl, C1-C20 allyl, C1-C20 alkoxy, C1-C26 arylalkyl, and C1-C26 arylalkoxy; and n is 1, 2, or 3.

4. The method of claim 1, wherein said at least one cyclic ester comprises a lactone of Formula IIa and/or IIb:

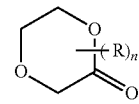

(IIa)

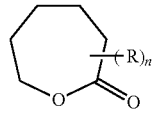

(IIb)

wherein each R is independently selected from H, hydroxyl, C1-C20 alkyl, C1-C20 allyl, C1-C20 alkoxy, C1-C26 arylalkyl, and C1-C26 arylalkoxy; and n is 1, 2, 3 or 4.

5. The method of claim 1, wherein said at least one cyclic ester comprises a cyclic carbonate of Formula IIIa and/or IIIb:

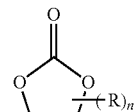

(IIIa)

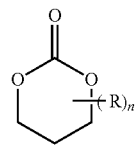

(IIIb)

wherein each R is independently selected from H, hydroxyl, C1-C20 alkyl, C1-C20 allyl, C1-C20 alkoxy, C1-C26 arylalkyl, and C1-C26 arylalkoxy; and n is 1, 2, or 3.

6. The method of claim 1, wherein said ring-opening polymerization initiator is selected from the group consisting of alcohols, trialkyl borates, trialkoxy borates, and tris(trimethylsilyl) borate.

7. The method of claim 1, wherein said ring-opening polymerization catalyst is selected from the group consisting of Tin(II) octoate, metal carboxylates, metal acetylacetonate, dibutyl tin(IV) dilaurate, organophosphoric acids, basic organocatalysts, tertiary amines, phosphines, N-heterocyclic carbenes (NHCs), and catalyst pairs based on bifunctional organocatalysis with thiourea-tertiary amines.

8. The method of claim 1, wherein said three-dimensional object comprises a copolymer.

9. The method of claim 1, wherein said three-dimensional object is a biomedical implant.

10. The method of claim 1, wherein said filler is present and comprises a bioactive agent.

11. The method of claim 1, said monomers and/or prepolymers polymerizable by exposure to actinic radiation or light comprising reactive end groups selected from the group consisting of acrylates, methacrylates, α-olefins, N-vinyls, acrylamides, methacrylamides, styrenics, epoxides, thiols, 1,3-dienes, vinyl halides, acrylonitriles, vinyl esters, maleimides, and vinyl ethers.

12. The method of claim 1, wherein said light absorbing pigment or dye is present and is:
    (i) titanium dioxide,
    (ii) carbon black, and/or
    (iii) an organic ultraviolet light absorber.

13. The method of claim 1, wherein said diluent is present and comprises an acrylate, a methacrylate, a styrene, an acrylic acid, a vinylamide, a vinyl ether, a vinyl ester, polymers containing any one or more of the foregoing, or a combination of two or more of the foregoing.

14. The method of claim 1, wherein said cyclic ester dual cure resin comprises:
   (i) from 0.1 to 4 percent by weight of said photoinitiator;
   (ii) from 10 to 40, 60, or 90 percent by weight of said monomers and/or prepolymers that are polymerizable by exposure to actinic radiation or light;
   (iii) from 0.001 to 5 percent by weight of said light absorbing pigment or dye when present;
   (iv) from 10, 20, 40 or 50 to 60, 80 or 90 percent by weight of said at least one cyclic ester;
   (v) from 0.001, 0.01 or 0.1 to 2, 4, 6 or 8 percent by weight of said ring-opening polymerization initiator;
   (vi) from 0.001, 0.01, or 0.1 to 2, 4, 6 or 8 percent by weight of said ring-opening polymerization catalyst;
   (vii) from 1 to 40 percent by weight of said diluent when present; and
   (viii) from 1 to 50 percent by weight of said filler when present.

15. The method of claim 1, wherein said forming step is carried out by additive manufacturing.

16. The method of claim 1, wherein said forming step is carried out:
   (i) by either bottom-up three-dimensional fabrication between a carrier and a build surface or top-down three-dimensional fabrication between a carrier and a fill level, the fill level optionally defined by a build surface;
   (ii) optionally with a stationary build surface;
   (iii) optionally while maintaining the resin in liquid contact with both the intermediate and the build surface, and
   (iv) optionally with said forming step carried out in a layerless manner, each during the formation of at least a portion of the three-dimensional intermediate.

17. The method of claim 1, wherein said forming step is carried out by continuous liquid interface production (CLIP).

18. The method of claim 1, wherein said forming step is carried out between a carrier and a build surface, and said method further comprises vertically reciprocating said carrier with respect to the build surface to enhance or speed the refilling of the build region with the polymerizable liquid.

19. The method of claim 1, wherein said three-dimensional object comprises a polymer blend, interpenetrating polymer network, semi-interpenetrating polymer network, or sequential interpenetrating polymer network.

20. The method of claim 1, wherein said heating step is carried out at least a first temperature and a second temperature,
   wherein said first temperature is greater than room temperature, said second temperature greater than said first temperature, and said second temperature is less than 300° C.

21. An intermediate product produced by a method comprising:
   (a) providing a cyclic ester dual cure resin;
   (b) forming a three-dimensional intermediate from said resin, where said intermediate has the shape of, or a shape to be imparted to, said three-dimensional object, and where said resin is solidified by exposure to light; and
   (c) optionally washing the three-dimensional intermediate,
   wherein said cyclic ester dual cure resin comprises:
      (i) a photoinitiator;
      (ii) monomers and/or prepolymers that are polymerizable by exposure to actinic radiation or light;
      (iii) optionally, a light absorbing pigment or dye;
      (iv) at least one cyclic ester;
      (v) a ring-opening polymerization initiator;
      (vi) a ring-opening polymerization catalyst;
      (vii) optionally a diluent; and
      (viii) optionally a filler.

22. The method of claim 1, wherein said three-dimensional object comprises a copolymer selected from the group consisting of:
   poly(l-lactide-co-glycolide) (PLG) (also referred to as poly(lactic-co-glycolic acid) or PLGA);
   poly(l-lactide-co-epsilon-caprolactone) (PLLC or PLCL); and
   poly(l-lactide-co-glycolide-co-epsilon-caprolactone) (PLGC).

* * * * *

UNITED STATES PATENT AND TRADEMARK OFFICE
CERTIFICATE OF CORRECTION

PATENT NO. : 10,774,177 B2
APPLICATION NO. : 16/674702
DATED : September 15, 2020
INVENTOR(S) : Gu et al.

Page 1 of 1

It is certified that error appears in the above-identified patent and that said Letters Patent is hereby corrected as shown below:

In the Specification

Column 7, Line 24: Please correct "NANOPDX®" to read -- NANOPOX® --

In the Claims

Column 18, Line 3, Claim 4, Formula IIa: Please correct " 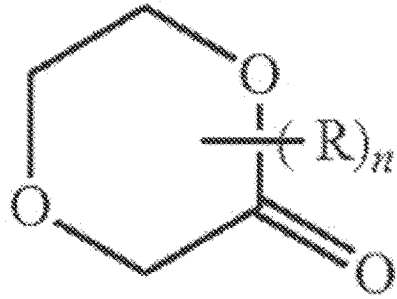 " to read

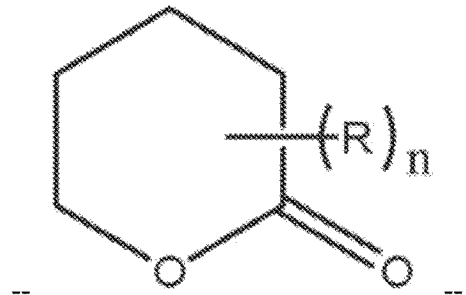 --

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*